United States Patent [19]  
Klug et al.

[11] Patent Number: 4,940,817  
[45] Date of Patent: Jul. 10, 1990

[54] PROCESS FOR THE PREPARATION OF N-ALKYLANILINES

[75] Inventors: Günter Klug, Monheim; Hans-Josef Buysch, Krefeld; Lothar Puppe, Burscheid, all of Fed. Rep. of Germany

[73] Assignee: Bayer Aktiengesellschaft, Leverkusen, Fed. Rep. of Germany

[21] Appl. No.: 301,672

[22] Filed: Jan. 25, 1989

[30] Foreign Application Priority Data

Feb. 6, 1988 [DE] Fed. Rep. of Germany ....... 3803662

[51] Int. Cl.$^5$ .................. C07C 87/52; C07C 88/02
[52] U.S. Cl. ..................... 564/305; 564/470
[58] Field of Search ................. 564/305, 470

[56] References Cited

U.S. PATENT DOCUMENTS 3,130,007  4/1964  Breck ........................... 502/79
3,702,886  11/1972  Argmer et al. ................. 502/61
4,300,011  11/1981  Rollmann ....................... 585/470

FOREIGN PATENT DOCUMENTS 45554  3/1985  Japan ............................ 564/305

OTHER PUBLICATIONS

*Chemical Abstracts* 103:104,685p, "N-monoalkylanilines", p. 595 (1985).
M. Windholz, ed., "The Merck Index", 10th Ed., p. 1454, Merck & Co., Inc., Rahway, NJ (1983).
*Acta. Chim. Hang.*, 20 (1959), p. 321.

*Primary Examiner*—Glennon H. Hollrah
*Assistant Examiner*—Mark W. Russell
*Attorney, Agent, or Firm*—Sprung, Horn, Kramer & Woods

[57] ABSTRACT

N-Alkylanilines can be prepared by reaction of anilines with N,N-dialkylanilines in the gas or liquid phase at elevated temperature by carrying out the reaction in the presence of zeolites.

18 Claims, No Drawings

PROCESS FOR THE PREPARATION OF N-ALKYLANILINES

BACKGROUND OF THE INVENTION

The present invention relates to a process for the preparation of N-alkylanilines, in which anilines which are not substituted on the N atom are reacted with N,N-dialkylanilines in the presence of zeolites at elevated temperature.

N-Monoalkylated anilines are important industrial intermediates for the preparation of dyestuffs, stabilizers, urethanes or ureas. They are prepared by alkylation of anilines with alcohols or the corresponding dialkyl ethers in the presence of acid catalysts, for example in the presence of phosphorous oxychloride, under pressure. However, not the pure monoalkylated anilines were produced by this way, but always also N,N-dialkylanilines to a large extent (Ullmanns Encyclopädie der technisechen Chemie (Ullmann's Encyclopaedia of Industrial Chemistry), 4th edition, Vol. 7 (1974), p. 572 ff.).

The ratio of monoalkylated to dialkylated anilines, such as is obtained in these preparation processes, thus, however, not always conforms to the particular demand. In general, the monoalkylated anilines are the more desirable products, which at the same time are more difficult to obtain. Moreover, N,N-dialkylanilines can be obtained in good yields by special processes. It is therefore desirable to render the ratio of monoalkylated to dialkylated anilines more flexible, that is, to have an efficient process for converting N,N-dialkylanilines into N-monoalkylanilines available. According to Acta Chim. Hung. 20 (1959), 321, transalkylation between N,N-diethylaniline and aniline can be achieved by passing the two reactants at elevated temperature in the gas phase over $Al_2O_3$. However, this transalkylation proceeds very slowly. At a space velocity of 0.25 ml/ml of catalyst/h at 250° C., only 0.16 mol % are converted. If the temperature is increased to accelerate the reaction, the conversion of N,N-diethylaniline is increased, but more and more ring-alkylated products appear and aniline is practically not alkylated on the N atom (loc. cit., p. 322, Table II). If at 280° C. the space velocity is only slightly increased, the conversion drops noticeably and yet non-negligible amounts of ring-alkylated products are formed (loc. cit., p. 323, Table III).

JP No. 60/045,552-A proposes to carry out the transalkylation between N,N-dimethylaniline and aniline in the presence of considerable amounts of concentrated sulphuric acid and a large excess of aniline at 180° to 300° C. in an autoclave. This reaction requires several hours; the $H_2SO_4$ catalyst has to be neutralized (disposed of) with alkali, and gets lost; finally the conversion is still incomplete despite a large amount of catalyst and excess of aniline. Furthermore, a reaction under pressure is in general associated with particular technical expenditure and, in the present case, also with corrosion risks.

SUMMARY OF THE INVENTION

It has now been found that the transalkylation can be carried out much more rapidly and selectively in the presence of alumosilicates of the zeolite type at temperatures between 200° and 350° C. The reaction proceeds smoothly with high conversions and virtually without ring-alkylation.

Accordingly, a process for the preparation of N-alkylanilines of the formula

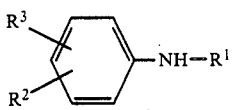  (I)

by reaction of anilines with N,N-dialkylanilines wherein these anilines and dialkyanilines are of the formulae

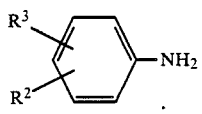  (II)

or

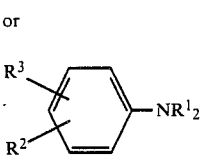  (III)

in which formulae
$R^1$ denotes $C_1$-$C_4$-alkyl and
$R^2$ and $R^3$, independently of one another, stand for hydrogen, $C_1$-$C_4$-alkyl, $C_1$-$C_4$-alkoxy, fluorine, chlorine or bromine, in the gas or liquid phase at elevated temperatures has been found, which is characterized in that the reaction is carried out in the presence of zeolites at temperatures of 200° to 350° C., preferably 220° to 330° C., particularly preferably 230° to 320° C.

DETAILED DESCRIPTION OF THE INVENTION

Zeolites are crystalline alumosilicates having the following general oxidic formula:

$$M_{m/z}[mAlO_2 \cdot nSiO_2] \cdot qH_2O \quad (IV)$$

in which
n/m represents the Si/Al ratio,
$M_{m/z}$ denotes exchangeable cations, in which
z indicates the valence of the cation and
q indicates the amount of the adsorbed water phase.

Different zeolite types or structures are described, for example, in D. W. Breck, Zeolite Molecular Sieves, John Wiley and Sons Inc., New York 1974. In these zeolites, the aluminum can be further replaced in part by other trivalent ions such as, for example, B (III), Fe(III) or Ga (III).

In the case of synthetic zeolite structure types, which are obtained by using organic additives, calcination to remove organic radicals is required before the preparation of the exchanged forms to be used according to the invention. The H form of the zeolites according to the invention can be prepared by ammonium exchange followed by calcination or by hydrogen ion exchange by means of mineral acids. Other cations in the zeolites to be used according to the invention are for example: $Na^\oplus$, $K^\oplus$, $Li^\oplus$, $Ca^{2+}$, $Mg^{2+}$, $Ba^{2+}$, $Zn^{2+}$, $Cu^{2+}$, $Ag^+$, $Ga^{3+}$, $La^{3+}$, $Ce^{3+}$, $Fe^{3+}$, $Ni^{2+}$, $Ti^{4+}$, $Zr^{4+}$, $Mn^{2+}$, $Sn^{2+}Cr^{3+}$, $Co^{2+}$, preferably $Na^+$, $K^+$, $Li^+$, $Ca^{2+}$, $Mg^{2+}$, $Zn^{2+}$, $Cu^{2+}$, $La^{3+}$, $Ce^{3+}$, $Fe^{3+}$, $Ni^{2+}$, $Sn^{2+}$.

According to the invention, in particular zeolites having an Si/Al ratio n/m $\geq$ 1 are used. Furthermore according to the invention, zeolites having a pore diameter $\geq 5$ Å are used.

The formula (IV) includes, for example, zeolites of the structure type zeolite L, faujasite, mazzite, mordenite, offretite, cancrinite, gmelinite, ZSM 12, ZSM 25, ferrierite, zeolite β, zeolite Y, ZSM 5, ZSM 11, ZSM 22, ZSM 23, ZSM 48, ZSM 43, PSH 3 and heulandite. Of these structure types, faujasite, zeolite L, ZSM 12 and mordenite are preferred. Zeolites of the structure type faujasite (such as, for example, zeolite Y) and zeolite L are particularly preferred.

Since the H+ forms of these zeolites have acidic properties, they are catalytically particularly effective. Furthermore, zeolites of the abovementioned structure types in which a portion of the exchangeable cations denote hydrogen ions, more than 50 equivalent %, particularly preferably at least 80 equivalent %, of the exchangeable cations being hydrogen ions, are therefore preferred according to the invention. The preparation of these partly acidic forms of zeolites by means of strong acids is prior art and therefore needs not to be discussed further. These processes are described, for example, in J. A. Rabo, Zeolite Chemistry and Catalysis, ACS Monograph 171, Washington D.C. 1976.

The transalkylation according to the invention can be carried out in such a manner that the reactants aniline and N,N-dialkylaniline or their ring-substituted derivatives are passed at temperatures above 200° C. in the form of gases, if necessary by using an inert carrier gas such as $N_2$, over one of the zeolite catalysts mentioned. The space velocity of the catalyst can be set to 0.1 to 8, preferably 0.2 to 5, particularly preferably 0.3 to 4, liters of mixture to be reacted per liter of zeolite per hour. However, the reaction can also be carried out in the liquid phase at temperatures above 200° C. under the resulting internal pressure. In this case, the amount of the zeolite catalyst is 2–50% by weight, preferably 5–40% by weight, particularly preferably 7–30% by weight, relative to the total weight of the batch. The variation of the process according to the invention in which the reaction is carried out in the gas phase is particularly elegant because it can generally be carried out in the absence of pressure, and therefore it is preferred.

For operation in gas phase reactors, the zeolites to be used according to the invention are made particulate. For this purpose, they are compacted with binders and granulated. Preferably, the binder materials used are $\gamma$-$Al_2O_3$ and $SiO_2$, for example in amounts of 15 to 50% by weight, relative to the ready-for-use zeolite catalysts.

The molar ratio of the reactants is not critical and can be 0.3 to 5, preferably 0.5 to 3, particularly preferably 0.8 to 1.5, moles of aniline to 1 mole of N,N-dialkylaniline.

It is furthermore possible to use inert solvents in addition, for example hydrocarbons such as benzene, toluene, xylene, benzine, cyclohexane, decalin and/or isooctane.

The starting materials for the process according to the invention to be reacted are those of the formulae (II) and (III). Preferred starting materials are those in which $R^{11}$ denoting $C_1$-$C_2$-alkyl takes the place of $R^1$. Further preferred starting materials are those in which $R^{12}$ and $R^{13}$, independently of one another denoting hydrogen, $C_1$-$C_2$-alkyl, $C_1$-$C_2$-alkoxy, fluorine or chlorine or particularly preferably $R^{22}$ and $R^{23}$ independently of one another denoting hydrogen or $C_1$-$C_2$-alkyl take the places of $R^2$ and $R^3$. Further preferred starting materials are those in which $R^3$ is hydrogen.

Example 1

0.5 mole each of aniline and N,N-dimethylaniline were dissolved in 200 ml of benzene and heated with 20 g of one of the zeolites mentioned for 3 hours at 300° C. in an autoclave. The formation of N-methylaniline is shown by Table I below:

TABLE I

| No. | Zeolite | N-Methylaniline (% by weight) |
|---|---|---|
| 1.1 | H-ZSM 5 | 21 |
| 1.2 | H-ZSM 11 | 27 |
| 1.3 | Sn-ZSM 5 | 14 |
| 1.4 | H-mordenite | 32 |
| 1.5 | H—Y | 49 |

Table I shows the results of the transalkylation obtained in batchwise operation and also shows the excellent catalytic action of the zeolites, in particular of H-ZSM 11, H-mordenite and in particular H-Y.

Example 2

A reaction tube, about 20 mm in diameter, was charged with 20 g of zeolite granules each having about 30% by weight of binder and an average particle size of 1 to 2 mm. A mixture of aniline and N,N-dimethylaniline was evaporated and the vapour mixture was passed over the catalyst bed at different temperatures. Table II below shows the conversion to N-methylaniline. The composition of the reaction mixtures was determined by gas chromatography.

TABLE II

| No. | Catalyst | Molar/ratio A/DMA[2] | °C. | Space velocity h | ml/ml/h | % by weight[2] A | NMA | DMA | ring-alkylated |
|---|---|---|---|---|---|---|---|---|---|
| 2.1 | H-ZSM 11/γ-$Al_2O_3$ | 3:1 | 300 | 4 | 1.0 | 64 | 13 | 23 | 0 |
| 2.2 | H—Y/γ-$Al_2O_3$ | 1:1 | 250 | 4 | 1.0 | 28 | 31 | 41 | <0.1 |
| 2.3 | H—L/γ-$Al_2O_3$ | 1:1 | 250 | 4 | 1.0 | 29 | 29 | 42 | <0.3 |
| 2.4 | H—Y/$SiO_2$ | 1:1 | 250 | 4 | 1.0 | 30 | 27 | ~43 | ~0.5 |
| 2.5 | Y-$Al_2O_3$[1] | 1:1 | 300 | 8 | 1.0 | 42 | 1 | 57 | 0 |
| 2.6 | $SiO_2$ [1] | | 300 | | no conversion | | | | |

[1]These materials were used as binders for the abovementioned zeolites.
[2]A = aniline; NMA = methylaniline; DMA = N,N- dimethylaniline.

According to Table II, it can be seen that high transalkylation rates were achieved at a much higher space velocity than according to the prior art. Even without excess aniline, a large portion, that is, up to 40 mole %, of dimethylaniline was converted at as low as 250° C. Under these conditions, virtually no ring-alkylated products were formed. The materials ($SiO_2$, γ-$Al_2O_3$) which were used as binders for the zeolites did not ($SiO_2$) or only very slightly (γ-$Al_2O_3$) effect transalkylation under the conditions of the invention. Thus, experiments 2.5 and 2.6 are comparative experiments.

Example 3

N,N-Diethylaniline and aniline were passed over a zeolite catalyst as in Example 2 in a molar ratio of 1:1. Table III below shows the result:

TABLE III

| No. | Catalyst | Temperature in °C. | Space Velocity ml/ml/h | Product Distribution in % by weight | | | |
|---|---|---|---|---|---|---|---|
| | | | | A | NEA | DEA | ring-alkylated |
| 3.1 | H—Y/SiO$_2$ | 250 | 1,0 | 26 | 22 | 51 | <1% |
| 3.2 | H—Y/γAl$_2$O$_3$ | 250 | 1,0 | 25 | 26 | 48 | <1% |
| 3.3 | H—Y/SiO$_2$ | 300 | 1,0 | 19 | ~59 | 19 | 3,1 after 1 |
| 3.4 | H—Y/SiO$_2$ | 300 | 1,0 | 19 | ~59 | 21 | 1,5 after 5 |

$^{(1)}$A = aniline; NEA = N-ethylaniline; DEA = N,N-diethylaniline

In this case, too, a high selectivity of the γ-zeolites with respect to the formation of N-ethylaniline is observed. The proportion of ring-alkylated compounds, which in some cases is relatively high at the start of the reaction, drops to insignificant values over a short period of time without impairing the conversion in other ways. This is illustrated by the data in 3.3 and 3.4, where the percentage of ring-alkylated product drops from 3.1 to 1.5% by weight during the 5 hours of operation.

What is claimed is:

1. In a process for the preparation of N-alkylanilines of the formula

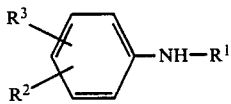

comprising reacting anilines of the formula

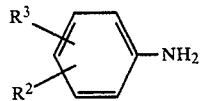

with N,N-dialkylanilines of the formula

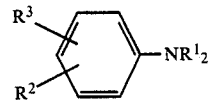

wherein
R$^1$ denotes C$_1$–C$_4$-alkyl and
R$^2$ and R$^3$, independently of one another, stand for hydrogen, C$_1$–C$_4$-alkyl, C$_1$–C$_4$-alkoxy, fluorine, chlorine or bormine,
in the gas or liquid phase at elevated temperatures, the improvement wherein the reaction is carried out in the presence of zeolites at temperatures of 200° to 350° C.

2. The process of claim 1 wherein the reaction is carried out at 220° to 330° C.

3. The process of claim 2 wherein the reaction is carried out at 230° to 320° C.

4. The process of claim 1, wherein the zeolites are of the formula:

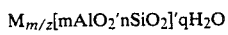

$$M_{m/z}[mAlO_2 \cdot nSiO_2] \cdot qH_2O$$

in which
n/m represents the Si/Al ratio,
M$_{m/z}$ denotes exchangeable cations, in which
z indicates the valence of the cation and
q indicates the amount of the adsorbed water phase.

5. The process of claim 4, wherein the Si/Al ratio n/m is >1.

6. The process of claim 1 wherein the zeolites have a pore diameter of >5A.

7. The process of claim 4, wherein the zeolites are of the structure type zeolite L, faujasite, mazzite, mordenite, offretite, cancrinite, gmelinite, ZSM 12, ZSM25, ferrierite, zeolite β, zeolite Y, ZSM 5, ZSM 11, ZSzm 22, ZSM 23, ZSM 48, ZSM 43, PSH 3 or heulandite.

8. The process of claim 7, wherein the zeolites are of the structure type faujasite, zeolite β, zeolite L, ZSM 12 or mordenite.

9. The process of a claim 8, wherein the zeolites are of the structure type and zeolite L.

10. The process of claim 4, wherein a portion of the exchangeable cations are hydrogen.

11. The process of claim 10, wherein >50 equivalent % of the exchangeable cations are hydrogen ions.

12. The process of claim 11 wherein >80 equivalent % of the exchangeable cations are hydrogen ions.

13. The process of claim 1, wherein the reaction is carried out at a space velocity of 0.1 to 8 liters of mixture to be reacted per liter of zeolite per hour.

14. The process of claim 13 wherein the space velocity is 0.2 to 5 liters of mixture to be reacted per liter of zeolite per hour.

15. The process of claim 14 wherein the space velocity is 0.3 to 4 liters of mixture to be reacted per liter of zeolite per hour.

16. The process claim 1, wherein molar ratio is 0.3 to 5 moles of aniline/mole N,N-dialkylaniline in the mixture to be reacted.

17. The process of claim 16 wherein the molar ratio is 0.5 to 3 moles of aniline/mole of N,N-dialkylaniline.

18. The process of claim 17 wherein the molar ratio is 0.8 to 1.5 moles of aniline/mole of N,N-dialkylaniline.

* * * * *